(12) United States Patent
Cegla

(10) Patent No.: US 10,556,073 B2
(45) Date of Patent: Feb. 11, 2020

(54) THERAPY DEVICE FOR TREATMENT OF RESPIRATORY DISEASES

(71) Applicant: R. Cegla GmbH & Co. KG, Montabaur (DE)

(72) Inventor: Ulrich Cegla, Montabaur (DE)

(73) Assignee: R. Cegla GmbH & Co. KG, Montabaur (DE)

( * ) Notice: Subject to any disclaimer, the term of this patent is extended or adjusted under 35 U.S.C. 154(b) by 948 days.

(21) Appl. No.: 14/780,093

(22) PCT Filed: Mar. 19, 2014

(86) PCT No.: PCT/EP2014/055479
§ 371 (c)(1),
(2) Date: Sep. 25, 2015

(87) PCT Pub. No.: WO2014/154541
PCT Pub. Date: Oct. 2, 2014

(65) Prior Publication Data
US 2016/0045689 A1    Feb. 18, 2016

(30) Foreign Application Priority Data
Mar. 26, 2013 (EP) .................................... 13161014

(51) Int. Cl.
*A63B 23/18*    (2006.01)
*A61M 16/00*    (2006.01)
(Continued)

(52) U.S. Cl.
CPC .... *A61M 16/0006* (2014.02); *A61M 16/0418* (2014.02); *A61M 16/0488* (2013.01);
(Continued)

(58) Field of Classification Search
CPC .............. A61M 16/0006; A61M 16/20; A61M 16/208; A61M 15/0086; A61M 39/10;
(Continued)

(56) References Cited

U.S. PATENT DOCUMENTS 4,403,616 A * 9/1983 King ...................... A63B 23/18
                                                       482/13
4,557,261 A    12/1985 Rugheimer
(Continued)

FOREIGN PATENT DOCUMENTS

EP    0009667    4/1980
EP    0134847    3/1985
(Continued)

*Primary Examiner* — Tu A Vo
(74) *Attorney, Agent, or Firm* — Pandiscio & Pandiscio

(57) ABSTRACT

A therapeutic device (1) for the treatment of human respiratory illnesses, with a mouthpiece (2) in which a passage duct (3) is worked, a hose (5), formed from a flexible elastic material, attached to the mouthpiece (2) arranged flush with the opening (6) of the passage duct (3), the free end (7) of which facing away from the passage duct (3) is open, a support body (11) connected to the mouthpiece (2) with a curved or bent cross-sectional structure, and an adjusting device (12) provided at a distance from the mouthpiece (2) in the support body (11), which can be moved in relation to the support body (11), which is connected to the hose (5) either directly or via intermediate elements (13), whereby the curvature of the hose (5) can be set independently from the radius of curvature of the support body (11).

14 Claims, 5 Drawing Sheets

(51) Int. Cl.
*A63B 21/00* (2006.01)
*A63B 21/008* (2006.01)
*A61M 16/04* (2006.01)

(52) U.S. Cl.
CPC .... *A63B 21/00069* (2013.01); *A63B 21/0085* (2013.01); *A63B 21/00196* (2013.01); *A63B 23/18* (2013.01); *A61M 2205/0216* (2013.01)

(58) Field of Classification Search
CPC .. A61M 39/1011; A61M 39/20; A61M 39/22; A61M 2039/242; A61M 2039/2426; A61M 2039/2433; A61M 2039/2344; A61M 2039/2493; A61M 2039/205; A61M 16/0488; A61M 16/0418; A61M 2205/0216; A63B 23/18; A63B 21/0085; A63B 21/00069; A63B 21/00196
USPC ..................... 482/11, 13, 111–113
See application file for complete search history.

(56) References Cited

U.S. PATENT DOCUMENTS

| | | | |
|---|---|---|---|
| 4,966,141 A | 10/1990 | Bacaner et al. | |
| 5,018,517 A * | 5/1991 | Liardet | A63B 23/18 128/200.24 |
| 5,193,529 A * | 3/1993 | Labaere | A63B 23/18 128/200.24 |
| 5,329,921 A | 7/1994 | Socaris et al. | |
| 5,427,089 A | 6/1995 | Kraemer | |
| 5,451,190 A * | 9/1995 | Liardet | A63B 23/18 128/200.24 |
| 5,569,122 A * | 10/1996 | Cegla | A63B 23/18 128/200.24 |
| 5,658,221 A * | 8/1997 | Hougen | A63B 23/18 482/13 |
| 5,890,998 A * | 4/1999 | Hougen | A61M 16/0006 482/13 |
| 5,899,832 A * | 5/1999 | Hougen | A63B 23/18 128/200.24 |
| 6,026,807 A | 2/2000 | Puderbaugh et al. | |
| 6,039,042 A | 3/2000 | Sladek | |
| 6,083,141 A * | 7/2000 | Hougen | A61M 16/0006 128/202.16 |
| 6,581,598 B1 * | 6/2003 | Foran | A61M 16/08 128/204.19 |
| 6,702,769 B1 * | 3/2004 | Fowler-Hawkins | A61H 23/0236 128/200.24 |
| 6,729,334 B1 | 5/2004 | Baran | |
| 6,984,214 B2 | 1/2006 | Fowler-Hawkins | |
| 7,775,211 B2 | 8/2010 | Wilson | |
| 7,900,625 B2 | 3/2011 | Kleinstreuer et al. | |
| 8,066,001 B2 | 11/2011 | Cegla | |
| 8,267,090 B2 | 9/2012 | Cegla | |
| 2008/0251069 A1 * | 10/2008 | Cegla | A63B 21/00196 128/200.24 |
| 2009/0159062 A1 * | 6/2009 | Bohman | A63B 21/0085 124/62 |
| 2009/0199853 A1 * | 8/2009 | Cegla | A61M 16/08 128/203.12 |
| 2012/0227741 A1 * | 9/2012 | Cegla | A63B 21/0088 128/205.12 |
| 2013/0160888 A1 | 6/2013 | Sheffer | |
| 2013/0184619 A1 * | 7/2013 | Von Hollen | A61M 16/00 601/46 |
| 2014/0238389 A1 | 8/2014 | Bruggemann et al. | |
| 2016/0045689 A1 | 2/2016 | Cegla | |

FOREIGN PATENT DOCUMENTS

| | | |
|---|---|---|
| EP | 0681853 | 11/1995 |
| EP | 1358901 | 11/2003 |
| EP | 1772165 | 4/2007 |
| EP | 1987864 | 11/2008 |
| EP | 2087927 | 8/2009 |
| EP | 2678060 | 4/2016 |
| FR | 2948288 | 1/2011 |
| WO | WO 98/24500 | 6/1998 |
| WO | WO 2007/002393 | 1/2007 |

* cited by examiner

THERAPY DEVICE FOR TREATMENT OF RESPIRATORY DISEASES

REFERENCE TO PENDING PRIOR PATENT APPLICATIONS

This patent application claims benefit of International (PCT) Patent Application No. PCT/EP2014/055479, filed 19 Mar. 2014 by R. Cegla GmbH & Co. KG for THERAPY DEVICE FOR THE TREATMENT OF RESPIRATORY DISEASES, which claims benefit of European Patent Application No. EP 13 161 014.9, filed 26 Mar. 2013, which patent applications are hereby incorporated herein by reference.

FIELD OF THE INVENTION

The present invention relates to a therapeutic device for the treatment of respiratory illnesses.

BACKGROUND OF THE INVENTION

A therapeutic device of this kind has been disclosed in EP 2 087 927 B1 which is used for the treatment of respiratory illnesses of persons. Such oscillating PEP systems generate rhythmical vibrations during exhalation due to the resulting pressure fluctuations, by means of which the airways are expanded and the mucous is separated from the bronchial walls.

Such respiratory therapy devices normally comprise a mouthpiece that is inserted in the human mouth and through which the breathing air is forced into a flexible elastic hose fixed onto the mouthpiece. The mouthpiece and the hose in this case are inserted in a curving pipe section that is fixed onto the mouthpiece. As a result of the curvature of the pipe section, the hose is shaped correspondingly to the radius of curvature of the pipe section, meaning that the passage cross-section of the hose is reduced in an area, as a result of which a higher air resistance is generated in this area. Furthermore, during exhalation, the free end of the hose is moved to and fro between the inner walls of the pipe section, thereby producing the necessary pressure fluctuations, since this guarantees that the air resistance in the curved area of the hose is changed slightly.

Such respiratory therapeutic devices have proven outstandingly effective in practice and are used successfully for corresponding bronchial illnesses. However, the airways become smaller and smaller in the direction of the lung periphery, ultimately reducing to a diameter of only about 0.5 mm, meaning that low frequencies between 2 and 6 Hz are necessary in order to overcome the impedance of the airways. For this reason, high pressures of about 10 to 15 cm $H_2O$ are required to overcome the capillary effects of the small airways in case of inflammations.

Although respiratory therapeutic devices of prior art have a mouthpiece with a position that can be changed in relation to the pipe section, such medical requirements cannot be achieved with the respiratory therapeutic devices which have been disclosed up to this point.

EP 1 987 864 A1 discloses a therapeutic device comprising a mouthpiece with a passage duct. In this case, a flexible elastic hose is attached to the opening of the passage duct and is supported by a support plate that is attached to the mouthpiece. At the free end of the support plate, a swivel joint is provided by means of which the resistance body can be variably adjusted to different angle positions in relation to the support plate.

It is a disadvantage that the change in position of the angle body exclusively changes the radii of curvature of the hose in the area of the swivel joint, meaning that only low oscillation frequencies can be achieved.

The task of the present invention is therefore to create a respiratory therapeutic device of the aforementioned kind by means of which both low and medium frequencies and pressure or flow fluctuations can be established during exhalation and varied within the widest possible range.

Furthermore, it is the task of the respiratory therapeutic device to enable a combination of the Positive Expiratory Pressure of prior art, by means of which a positive pressure status is generated within the mouthpiece of the respiratory therapeutic device.

SUMMARY OF THE INVENTION

This task is accomplished by the provision and use of a novel therapeutic device for the treatment of respiratory illnesses, as will hereinafter be discussed in further detail.

Due to the fact that the support body has an adjusting device attached to it which is held relative to the rigid support body in such a way as to be movable on it, and as a result of which the adjusting device is in an active connection with the hose either directly or via intermediate elements, a corresponding change in the adjustment direction makes it possible to set or change the distance from the hose to the support body, as a result of which the curvature of the hose can be set and varied. Such a change in the curvature of the hose also changes the frequency of the exhaled breathing air and changes the pressure with which the hose counteracts the throughflow of exhaled breathing it in the form of air resistance. As a result, a corresponding change in the adjustment direction enables the frequency of the hose as well as the pressure status of the hose to be adapted to the specified medical conditions. Although these medical conditions have been known in the specialist world for many years, no solution has been found for a respiratory therapeutic device by means of which the medically required frequencies and pressures can be set during exhalation of the breathing air in such a way that a corresponding expectorant effect is achieved in the lung periphery. The respiratory therapeutic devices that have been disclosed can thus only treat the bronchial mucus in the larger area of the lungs with the pressures and vibrations that can be set.

The drawing shows three sample embodiments of a respiratory therapeutic device configured in accordance with the present invention, the details of which are explained below. In the drawing,

DETAILED DESCRIPTION OF THE PREFERRED EMBODIMENT

Figure 1:
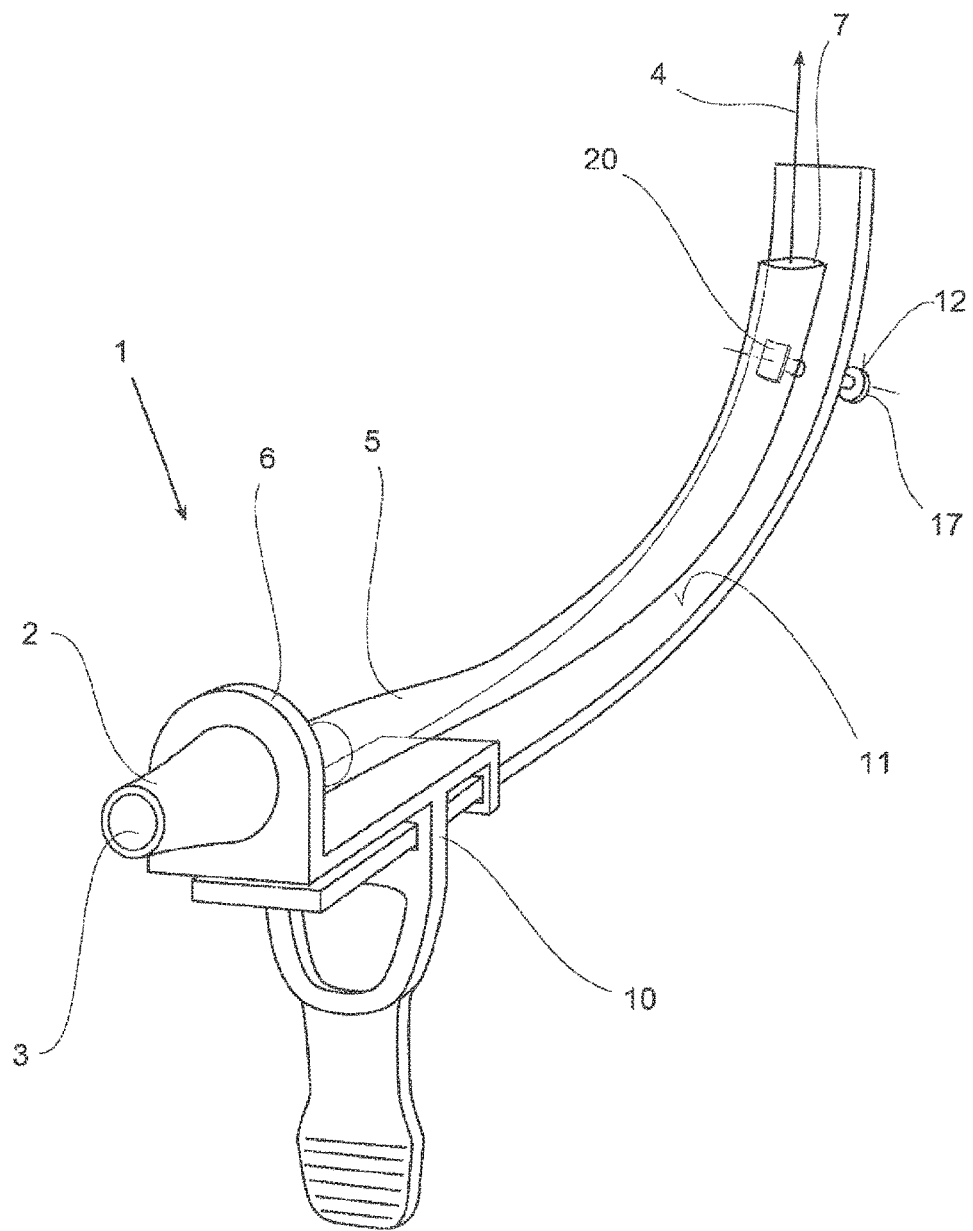
FIG. 1 shows a first embodiment of a respiratory therapeutic device consisting of a mouthpiece in which a passage duct is worked, of a flexible elastic hose attached to the mouthpiece flush with the passage duct and of a support body with a curved structure, and in which an adjusting device is inserted at a distance from the mouthpiece interacting with the hose, as a perspective view.

FIG. 1 shows a therapeutic device 1 for the treatment of respiratory illnesses that can be used as a medicinal device for generating low to medium-frequency pressure and flow fluctuations during the exhalation of a person so as to treat the airways, in particular in the lung periphery, which has a diameter of about 0.5 mm. The respiratory therapeutic device 1 should be operated at a frequency of 2 to 6 Hz in order to overcome the impedance of the airways, as a result of which high pressures of about 10 to 15 cm $H_2O$ are generated. This enables a corresponding capillary effect in the lung peripheries to be overcome, as a result of which bronchial mucus is released in the event of inflammation and the bronchioles (small bronchial tubes) are expanded.

So as to allow the necessary frequencies and pressures to be set, the therapeutic device 1 comprises a mouthpiece 2 in which a passage duct 3 is worked. The mouthpiece 2 is normally arranged between the upper and lower lips of a person, and breathing air is blown through the passage duct 3 of the mouthpiece 2 as schematically indicated by arrows. The breathing air is identified with the reference number 4.

A hose 5 made from a flexible elastic material is fixed onto the mouthpiece 2 flush to the opening 6 in the passage duct 3, as a result of which the breathing air 4 is pressed into the hose 5. The hose 5 has a passage opening at its free end 7 facing away from the passage duct 3, which means that the breathing air 4 that has been pressed in flows out of the hose 5.

To initially bend the passage cross-section of the hose 5 within a particular specified area as a result of which it has a smaller passage cross-section than the linear area of the hose 5, a curved or bent support body 11 is provided that is firmly connected to the mouthpiece 2. The curvature of the support body 11 means that the flexible elastic hose 5 is deformed, with the effect that in the area of the curvature of the support body 11, the passage cross-section of the hose 5 is reduced in comparison to the linear area of the hose 5. Consequently, during exhalation, the breathing air 4 flows through the passage duct 3 into the hose 5, causing it to vibrate as the air flows out. In particular, the free end 7 of the hose 5 vibrates to and fro, and is only limited by the support body 11.

To change the frequencies and the pressures that are set which must be overcome by the breathing air 4 flowing through the hose 5 when the patient exhales, there is also an adjusting device 12 arranged in the support body 11 which can be moved relative to it. The adjusting device 12 can be configured either as a detent pin 16 or an adjusting screw 17 according to FIG. 2 or 3. The free end of the detent pin 16 or the adjusting screw 17 has a support plate 20 that is in an active contact with the hose 5 either directly or via intermediate elements 13.

Figure 2:
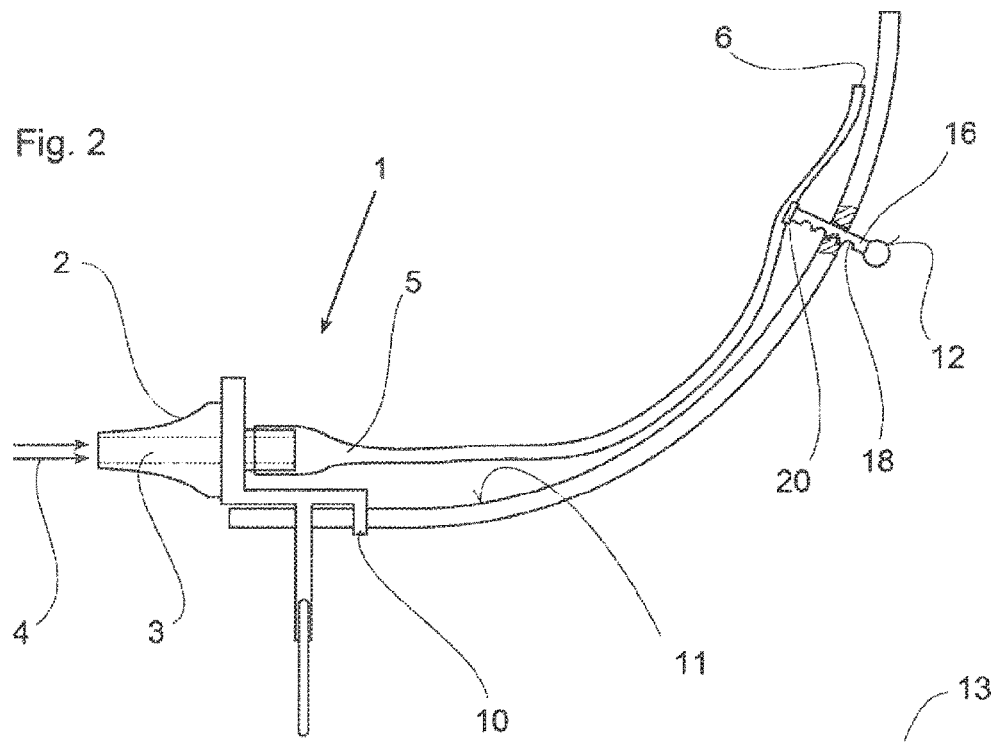
FIG. 2 shows the respiratory therapeutic device in accordance with FIG. 1, in a side view.

The change in position of the adjusting device 12 consequently varies the distance from the hose 5 to the support body 11, as a result of which the curvature of the hose 5 can be set irrespective of the radius of curvature of the support body 11. FIG. 2 shows the detent pin 16 of the adjusting device 12 arranged directly on the underside, i.e. the area facing the detent pin 16. The detent pin 16 is pushed into the detent groove 18 worked into the support body 11, and can be moved either in the direction of the hose 5 or opposite to it, allowing the curvature of the hose 5 to be changed.

Figure 3:
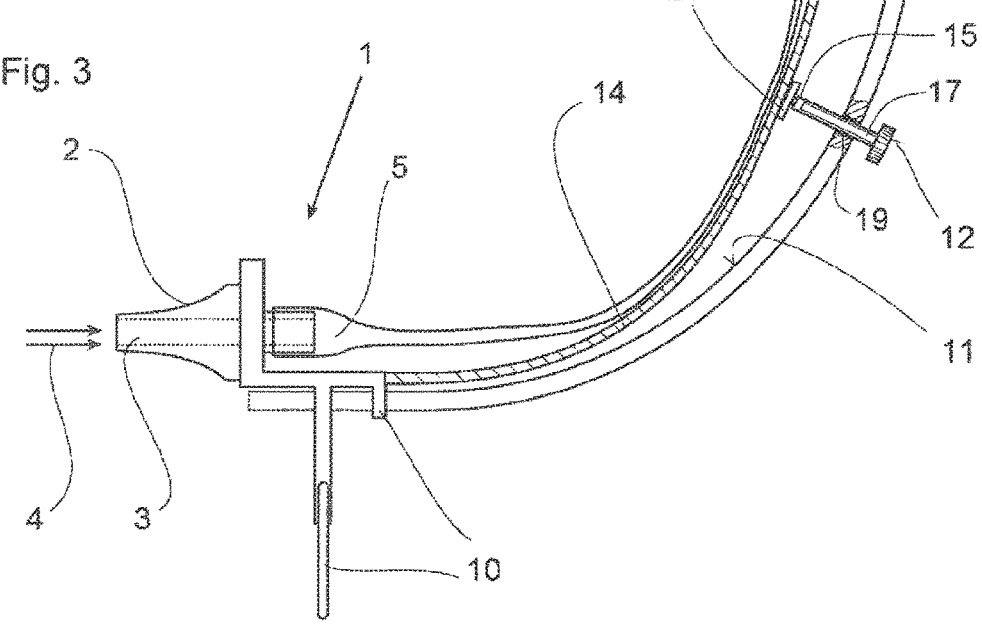
FIG. 3 shows a second embodiment of a respiratory therapeutic device consisting of a mouthpiece in which a passage duct is worked, of a flexible elastic hose attached to the mouthpiece flush with the passage duct and of a support body with a curved structure, and in which an adjusting device is inserted at a distance from the mouthpiece interacting with the hose, as a side view.

FIG. 3 shows the adjusting device 12 formed by an adjusting screw 17 that is screwed into an interior thread 19 worked into the support body 11. Furthermore, a guide plate 14 is provided between the support plate 20 of the adjusting screw 17 and the hose 5, serving as an intermediate element 13. The guide plate 14 is firmly connected to the mouthpiece 2 and consists of a flexible elastic material which can thus be deformed, as a result of which when the position of the adjusting screw 17 is changed, not only the guide plate 14 but also the hose 5 can be positioned at a closer or further distance from the support body 11. Furthermore, the guide plate 14 limits the vibration range of the free end 7 of the hose 5, because the hose 5 is supported by the guide plate 14 in an area, meaning that it can freely vibrate exclusively opposite to the plane formed by the guide plate 14.

Figure 4:
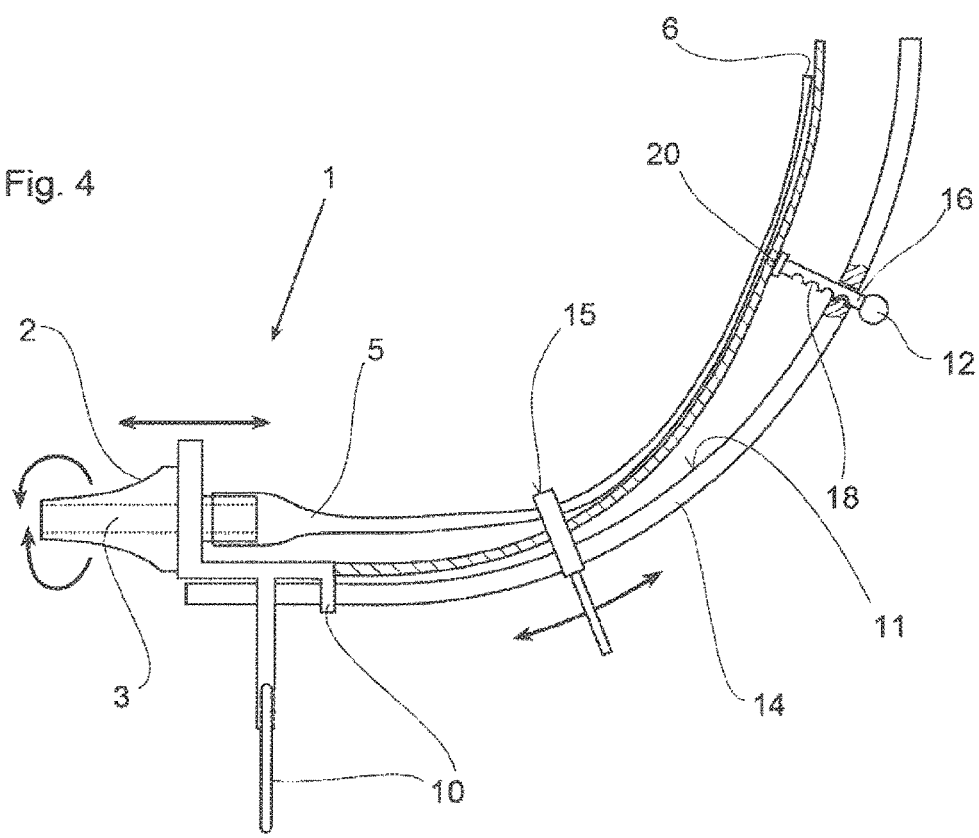
FIG. 4 shows the respiratory therapeutic device in accordance with FIG. 2 with a guide plate inserted between the hose and the adjusting device.

FIG. 4 shows that a holder 15 is provided on the support body 11 by means of which the position of the guide plate 14 on the support body 11 can be moved in relation to it.

The holder 15 namely consists of a holding piece that is mounted on the support body 11 so as to be movable, and of an articulation. As a result, not only can the distance from the guide plate 14 to the support body 11 be varied by means of the adjusting device 12, but so can the resulting distance between the adjusting device 12 and the point of rotation of the guide plate 14, meaning that the hose 5 can be given corresponding curvatures that are independent from the radius of curvature of the support body 11.

To allow the therapeutic device 1 to be held manually against the mouth of a patient, a holding device 10 is formed on the mouthpiece 2 or on the support body 11, projecting at right angles from it.

The adjusting device 12 or the detent pin 16 or the adjusting screw 17 largely run at right angles to the support body 11. However, it is conceivable for the axis of symmetry of the detent groove 18 or of the interior thread 19 to be worked into the support body 11 at an angle to its surface.

Figure 5:
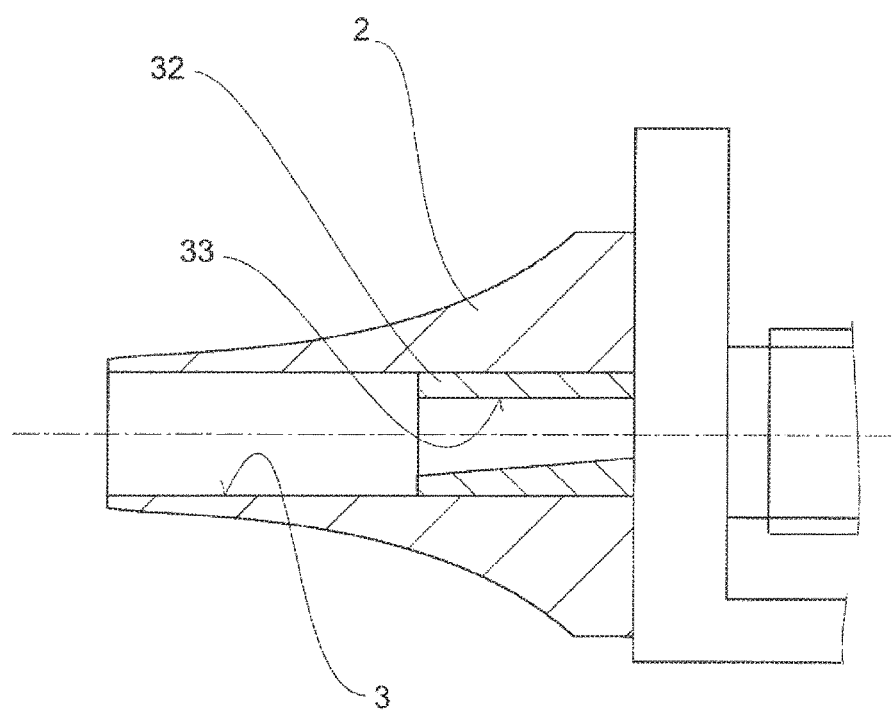
FIG. 5 shows a third embodiment of a respiratory therapeutic device consisting of a mouthpiece in which a passage duct is worked, the diameter of which is reduced by means of a plug with a smaller sized passage opening, of a flexible elastic hose attached to the mouthpiece flush with the passage duct and of a support body with a curved structure, and in which an adjusting device is inserted at a distance from the mouthpiece interacting with the hose, as a side view

The third sample embodiment of a respiratory therapeutic device 1 configured in accordance with the present invention and shown in FIG. 5 differs from the respiratory therapeutic device 1 shown in FIG. 1 in that a plug 32 is inserted into the passage duct 3 of the mouthpiece 2. The plug 32 has a cylindrical or funnel-shaped passage opening 33 worked into it, the interior diameter of which is significantly smaller than the interior diameter of the passage duct 3, as a result of which the plug 32 generates an increased air resistance by means of which the breathing air exhaled by the patient is compressed within the mouthpiece 2. This causes the pressure prevailing in the mouthpiece 2 to increase.

Figure 6A:
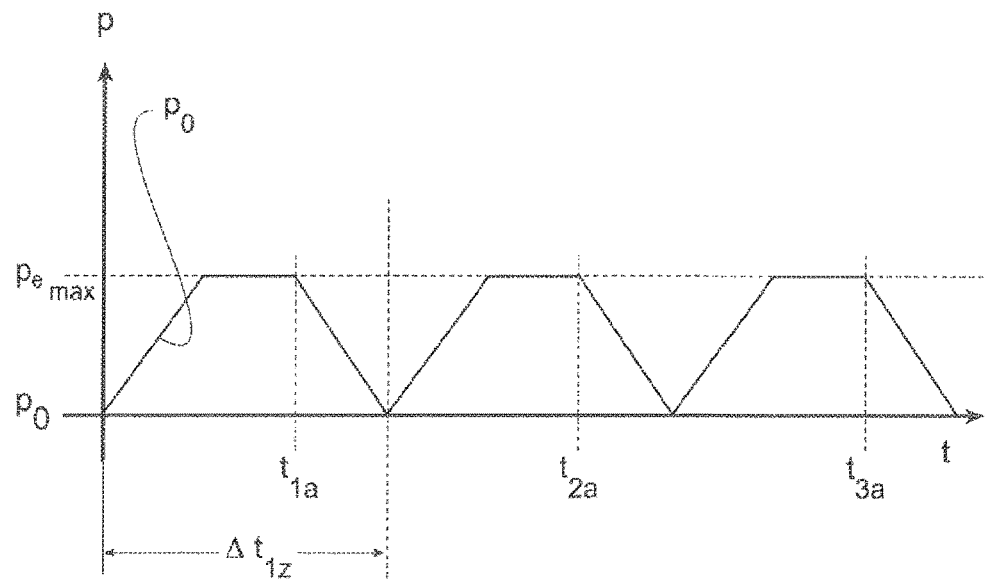
FIG. 6a shows a diagram of a pressure profile which can be generated with the respiratory therapeutic devices in accordance with FIGS. 1 and 3.

FIGS. 6a and 6a show in comparison which pressure profiles actually result during exhalation within the mouthpiece 2 in the different embodiments of the therapeutic device 1 shown in FIGS. 1 to 5. The respiratory therapeutic device 1 shown in FIGS. 1 to 4 generates a positive pressure when air is blown in, rising from zero ($P_0$) to a maximum pressure $P_{emax}$, and then dropping to $P_0$ in spite of further exhalation, only to rise back to $P_{emax}$ and fall to $P_0$ again. A different frequency and different pressure fluctuations are achieved according to the curvature of the hose 5.

Changing the elasticity and curvature of the support plate 20 and the position of the holder 15 also allows the shape of the pressure rise and pressure drop to be influenced, e.g. slow rise—fast drop, symmetrical rise and drop, fast rise—slow drop.

Figure 6B:
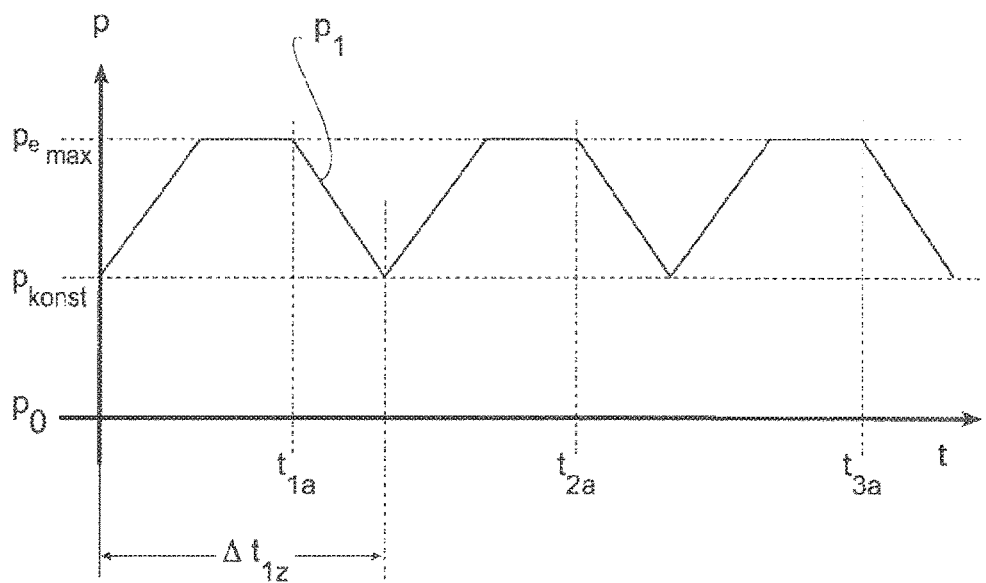
FIG. 6b shows a diagram of a pressure profile which can be generated with the respiratory therapeutic device in accordance with FIG. 5.

By means of the plug 32 according to the embodiment shown in FIG. 5, an increased pressure is generated throughout the entire exhalation, because the exhaled air is compressed in the passage duct 3 of the mouthpiece 2 by the plug 32 and its tapering or constricted interior contour 33. This continuously positive constant pressure $P_{const}$ flowing into the hose 5 of the exhalation device 1 shown in FIGS. 1 to 5 generates pressure fluctuations in this device which rise from $P_{const}$ to $P_{emax}$, and then immediately fall to $P_{const}$, only to rise back to $P_{emax}$ and fall again. This pressure profile is established throughout the entire exhalation procedure, and is shown in FIGS. 6a and 6b.

As a result, a continuously positive pressure is created which has pressure fluctuations modulated onto it. Here too, changes in the elasticity and curvature of the support plate 20 and the position of the holder 15 can change or individually set the profile of the pressure rise and pressure drop.

Furthermore, differently configured plugs 32 with differently designed interior contours 33 can be used. For example, the interior diameter of the passage opening 33 can be variably configured. It is also conceivable for the interior diameter not to be designed as a cylindrically shaped passage opening but rather as a tapering contour, for example in the form of a cone, by means of which a different kind of pressure status is achieved.

The invention claimed is:

1. A therapeutic device (1) for the treatment of human respiratory illnesses, said therapeutic device (1) comprising:
    a mouthpiece (2) having a distal end, a proximal end, and a passage duct (3) extending therebetween, said passage duct (3) having a distal opening on said distal end of said mouthpiece (2) and a proximal opening on said proximal end of said mouthpiece (2), and said passage duct (3) defining a longitudinal axis extending between said distal end of said mouthpiece (2) and said proximal end of said mouthpiece (2);
    a hose (5) formed out of a flexible elastic material, said hose (5) comprising a distal end, a proximal end, and a lumen extending therebetween, said proximal end of said hose (5) being mounted to said mouthpiece (2) with said proximal end of said hose (5) being aligned with said distal opening of said passage duct (3) such that said hose is fluidically connected to said passage duct (3), and such that said distal end of said hose is open to atmosphere;
    a support body (11) having a proximal portion mounted to said mouthpiece (2) and a distally-extending curved portion for supporting said hose (5) wherein said proximal portion of said support body extends distally from said mouthpiece in a direction that is parallel to said longitudinal axis of said mouthpiece, and said distally-extending curved portion of said support body (11) comprises an arc extending away from said longitudinal axis of said mouthpiece, said arc of said support body defining a radius of curvature; and
    an adjusting device (12) having a proximal end and a distal end, said adjusting device (12) passing through said distally-extending curved portion of said support body (11) at a distance from said mouthpiece (2) such that said distal end of said adjusting device (12) engages said hose; a guide plate (14) having a distal end, a proximal end, and a body extending therebetween, said body of said guide plate (14) being disposed between said distal end of said adjusting device (12) and said hose (5), such that said distal end of said adjusting device (12) contacts said body of said guide plate (14) and such that at least a portion of said hose (5) lies loose on said body of said guide plate (14); wherein
    said adjusting device (12) is configured to be selectively moved relative to said support body (11), such that a distance between said hose (5) and said support body (11), and a distance between said guide plate (14) and said support body (11) are configured to be selectively adjusted, whereby to selectively vary an arc of said hose relative to said longitudinal axis of said mouthpiece, said adjusting device being configured to adjust a radius of curvature of said guide plate independently to said radius of curvature of said distally-extending curved portion of said support body (11).

2. The therapeutic device in accordance with claim 1, wherein a plug (32) is disposed in said passage duct (3) intermediate said distal opening of said passage duct and said proximal opening of said passage duct, said plug (32) having a passage opening (33) passing through said plug (32) such that said distal opening of said passage duct (3) remains in fluid communication with said proximal opening of said passage duct when said plug (32) is disposed in said passage duct, and further wherein said passage opening (33) of said plug (32) comprises a proximal end and a distal end, the proximal end of said passage opening (33) having a diameter that is larger than a diameter of said distal end of said passage opening.

3. The therapeutic device in accordance with claim 1, wherein a plug (32) is disposed in said passage duct (3) intermediate said distal opening of said passage duct (3) and said proximal opening of said passage duct, wherein the plug (32) comprises a passage opening (33), wherein the diameter of said passage opening (33) of said plug varies along a length of said passage opening, and further wherein said passage opening of said plug comprises a geometry selected from the group consisting of: cylindrical, tapering, and funnel-shaped.

4. The therapeutic device in accordance with claim 1, wherein said adjusting device (12) passes through said distally-extending curved portion of said support body (11) perpendicular to a plane of said distally-extending curved portion of said support body (11) at a location where said adjusting device passes through said distally-extending curved portion of said support body.

5. The therapeutic device in accordance with claim 1, further comprising a holder (15) slidably mounted to said distal-extending curved portion of said support body (11), said holder (15) engaging said body of said guide plate (14) such that the curvature of said body of said guide plate (14) is configured to be selectively varied by sliding said holder relative to said distally-extending curved portion of said support body.

6. The therapeutic device in accordance with claim 1, wherein said adjusting device (12) is configured as a detent pin (16) having a plurality of detents formed along said adjusting device intermediate said proximal end and said distal end of said adjusting device, and further wherein said distally-extending curved portion of said support body (11) comprises a detent groove (18) at a location where said adjusting device (12) passes through said distally-extending curved portion of said support body (11), such that a detent of said adjusting device (12) is configured to be selectively moved into engagement with, or out of engagement with, said detent groove (18) of said support body (11).

7. The therapeutic device in accordance with claim 6, wherein said adjusting device (12) further comprises a support plate (20) mounted to said distal end of said adjusting device (12).

8. The therapeutic device in accordance with claim 7, wherein said support plate (20) comprises a geometry selected from the group consisting of: circular, elliptical, and polygonal.

9. The therapeutic device in accordance with claim 7, wherein said support plate (20) comprises a geometry selected from the group consisting of: circular, elliptical, and polygonal.

10. The therapeutic device in accordance with claim 1, wherein said support body (11) further comprises an outwardly projecting holding device (10).

11. The therapeutic device in accordance with claim 1, wherein said adjusting device (12) passes through said distally-extending curved portion of said support body (11) at an angle to a plane of said distally-extending curved portion of said support body (11) at a location where said adjusting device passes through said distally-extending curved portion of said support body.

12. The therapeutic device in accordance with claim 1, wherein said adjusting device (12) is configured as a screw having a screw thread formed thereon intermediate said proximal end and said distal end of said adjusting device, and further wherein said distally-extending curved portion of said support body (11) comprises a threaded hole at a location where said adjusting device (12) passes through said distally-extending curved portion of said support body (11), said threaded hole being configured to mate with said screw thread formed on said adjusting device, such that said adjusting device (12) is configured to be moved distally or proximally by selectively rotating said adjusting device (12).

13. The therapeutic device in accordance with claim 12, wherein said adjusting device (12) further comprises a support plate (20) mounted to said distal end of said adjusting device (12).

14. A therapeutic device (1) for the treatment of human respiratory illnesses, said therapeutic device (1) comprising:
a mouthpiece (2) having a distal end, a proximal end, and a passage duct (3) extending therebetween, said passage duct (3) having a distal opening on said distal end of said mouthpiece (2) and a proximal opening on said proximal end of said mouthpiece (2), and said passage duct (3) defining a longitudinal axis extending between said distal end of said mouthpiece and said proximal end of said mouthpiece (2);
a hose (5) formed out of a flexible elastic material, said hose (5) comprising a distal end, a proximal end, and a lumen extending therebetween, said proximal end of said hose (5) being mounted to said mouthpiece (2) with said proximal end of said hose (5) being aligned with said distal opening of said passage duct (3) such that said hose is fluidically connected to said passage duct (3), and such that said distal end of said hose is open to atmosphere;
a support body (11) having a proximal portion mounted to said mouthpiece (2) and a distally-extending curved portion for supporting said hose (5), wherein said proximal portion of said support body extends distally from said longitudinal axis of said mouthpiece in a direction that is parallel to said longitudinal axis of said mouthpiece, and said distally-extending curved portion of said support body (11) comprises an arc extending away from said longitudinal axis of said mouthpiece, said arc of said support body defining a radius of curvature;
an adjusting device (12) having a proximal end and a distal end, said adjusting device (12) passing through said distally-extending curved portion of said support body (11) at a distance from said mouthpiece (2) such that said distal end of said adjusting device (12) engages said hose;
a holder (15) slidably mounted to said distally-extending curved portion of said support body (11) such that said holder (15) engages said hose and holds said hose in close proximity to said support body (11) where said holder (15) contacts said hose;
wherein said adjusting device (12) is configured to be selectively moved relative to said support body (11), such that a distance between said hose (5) and said support body (11) is configured to be selectively adjusted, whereby to selectively vary an arc of said hose relative to said longitudinal axis of said mouthpiece, said adjusting device being configured to adjust a radius of curvature of said hose (5) independently to said radius of curvature of said distally-extending curved portion of said support body (11); and
wherein said holder (15) is configured to be selectively moved relative to said support body (11), such that the distance between said hose (5) and said support body (11) is configured to be selectively adjusted, whereby to further selectively vary said arc of said hose relative to said longitudinal axis of said mouthpiece and permit said hose to assume complex shapes comprising multiple curves.

* * * * *